(12) United States Patent  
Matter et al.

(10) Patent No.: US 7,399,118 B2  
(45) Date of Patent: Jul. 15, 2008

(54) THERMAL GAS FLOWMETER COMPRISING A GAS QUALITY INDICATOR

(75) Inventors: Daniel Matter, Brugg (CH); Rolf Luchsinger, Uster (CH); Beat Kramer, Windisch (CH); Bruno Sabbattini, Wettingen (CH)

(73) Assignee: EMS-Patent AG, Domat/EMS (CH)

( * ) Notice: Subject to any disclaimer, the term of this patent is extended or adjusted under 35 U.S.C. 154(b) by 0 days.

(21) Appl. No.: 10/524,948

(22) PCT Filed: Jul. 22, 2003

(86) PCT No.: PCT/CH03/00492

§ 371 (c)(1),
(2), (4) Date: Aug. 18, 2005

(87) PCT Pub. No.: WO2004/018976

PCT Pub. Date: Mar. 4, 2004

(65) Prior Publication Data

US 2006/0179936 A1    Aug. 17, 2006

(30) Foreign Application Priority Data

Aug. 22, 2002 (EP) ................... 02405715

(51) Int. Cl.
*G01K 17/00* (2006.01)
*G01N 25/00* (2006.01)

(52) U.S. Cl. ............... 374/36; 374/31; 374/32; 374/43; 73/25.01; 73/204.11; 73/25.05; 73/204.19; 73/23.31

(58) Field of Classification Search ............ 374/31, 374/36
See application file for complete search history.

(56) References Cited

U.S. PATENT DOCUMENTS 4,306,293 A * 12/1981 Marathe ............ 700/291

(Continued)

FOREIGN PATENT DOCUMENTS

EP      0 468 793 A3    5/1992

(Continued)

OTHER PUBLICATIONS

F. Mayer et al., Single-Chip CMOS Anemometer, Proc. IEEE, Intern. Electron Devices Meeting (IEDM, 1997) 895-898.

(Continued)

*Primary Examiner*—Gail Verbitsky
*Assistant Examiner*—Mirellys Jagan
(74) *Attorney, Agent, or Firm*—Marshall & Melhorn, LLC

(57) ABSTRACT

The invention relates to a method and a device for measuring a gas consumption by means of a gas meter. A gas meter with thermal mass flow sensor for determining mass flow signals ($S_M$) and with a calibration as energy meter for outputting energy value signals ($S_E$) is known. According to the invention, a gas type is determined by the gas meter insofar as combustible and non-combustible gas mixtures are differentiated. The gas meter is operated, in the case of a non-combustible gas mixture, with calibration in mass or standard volume units (l/min) and, in the case of a combustible gas mixture, with calibration in energy units (kWh). Embodiments concern inter alia: measurement of a gas parameter ($\lambda$, $\alpha$, c, $\eta$) of the gas or determining the gas type; gas quality sensor with an identical construction to thermal flow sensor; measuring intervals lengthened in the case of non-combustible gas and shortened in the case of combustible gas. Advantages are inter alia: reliable energy measurement because of automatic differentiation between non-meterable gas and high-quality useful gas; detection of manipulation attempts; and automatic heat value tracking even without heat value measurement.

13 Claims, 2 Drawing Sheets

U.S. PATENT DOCUMENTS

Figure 1:
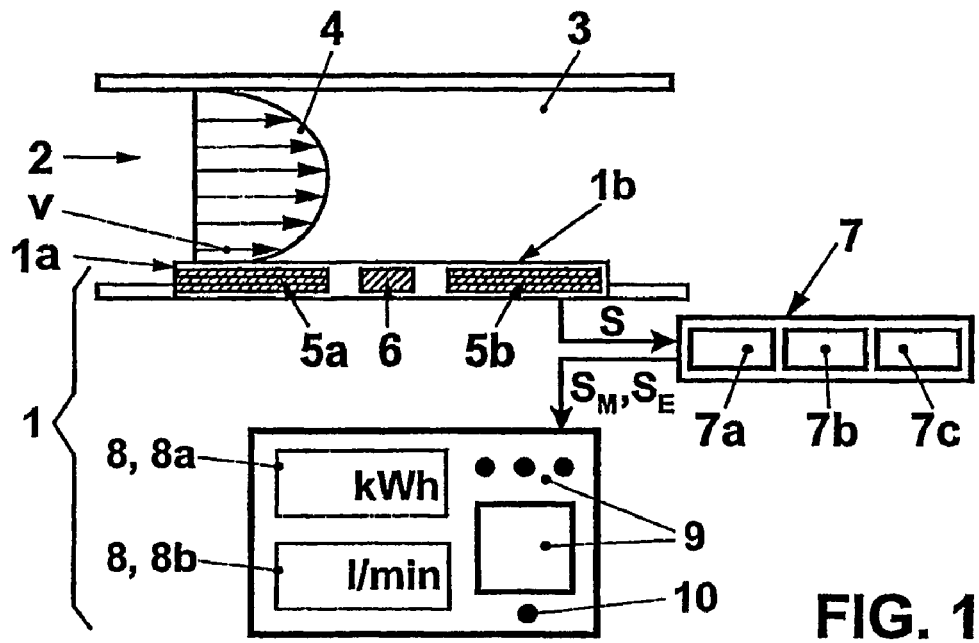

| | | | |
|---|---|---|---|
| 4,345,463 A * | 8/1982 | Wilson et al. | 374/36 |
| 4,396,299 A * | 8/1983 | Clingman et al. | 374/37 |
| 5,026,171 A * | 6/1991 | Feller | 374/41 |
| 5,201,581 A * | 4/1993 | Vander Heyden et al. | 374/36 |
| 5,226,728 A * | 7/1993 | Vander Heyden | 374/36 |
| 5,311,447 A | 5/1994 | Bonne | |
| 5,551,282 A * | 9/1996 | Vander Heyden | 73/30.03 |
| RE35,639 E * | 10/1997 | Vander Heyden et al. | 374/36 |
| 5,882,115 A * | 3/1999 | Vander Heyden et al. | 374/37 |
| 6,047,589 A | 4/2000 | Hammond et al. | |
| 6,244,097 B1 * | 6/2001 | Schley et al. | 73/23.2 |
| 6,279,380 B1 * | 8/2001 | Van Wesenbeeck et al. | 73/25.01 |
| 6,517,237 B1 * | 2/2003 | Hammond et al. | 374/31 |
| 6,612,186 B1 * | 9/2003 | Patten et al. | 73/861.04 |
| 6,963,809 B2 * | 11/2005 | Matter et al. | 702/45 |
| 2006/0123892 A1 * | 6/2006 | Brekelmans et al. | 73/61.76 |
| 2006/0212249 A1 * | 9/2006 | Matter et al. | 702/100 |

FOREIGN PATENT DOCUMENTS

| | | |
|---|---|---|
| EP | 0 373 965 A3 | 12/1999 |
| EP | 1 164 361 A1 | 12/2001 |
| FR | 2 776 776 A1 | 1/1999 |
| JP | 62280617 A * | 12/1987 |
| JP | 11118569 A * | 4/1999 |
| RU | 2125262 C1 | 1/1999 |
| WO | WO 01/18500 A1 | 3/2001 |
| WO | WO 01/96819 A1 | 12/2001 |

OTHER PUBLICATIONS

J. Robadey et al., Two Dimensional integrated gas flow sensors by CMOS IC technology, J. Mecromech. Micromeg. 5 (1995) 243-250.

F. Mayer et al., Scaling of thermal CMOS gas flow microsensors: experiment and simulation, Proc. IEEE Micro Electro Mechanical Systems, (IEEE, 1996), 116-121.

\* cited by examiner

| | Temperature: 300K; Pressure: 1.013 bar | | | |
|---|---|---|---|---|
| Gas | λ | $c_p$ | ρ | α |
| | W/(mK) | J/(kgK) | kg/m³ | m²/s |
| Methane | 0.0341 | 2200.34 | 0.653 | 2.37E-05 |
| Ethane | 0.0213 | 1749.25 | 1.231 | 9.90E-06 |
| Propane | 0.0180 | 1626.57 | 1.967 | 5.63E-06 |
| Carbon dioxide | 0.0168 | 842.99 | 1.797 | 1.11E-05 |
| Nitrogen | 0.0260 | 1038.77 | 1.138 | 2.20E-05 |
| Oxygen | 0.0263 | 918.78 | 1.301 | 2.20E-05 |
| Hydrogen | 0.1869 | 14285.71 | 0.082 | 1.60E-04 |
| Water | 0.0187 | 1865.11 | 0.767 | 1.31E-05 |
| Carbon monoxide | 0.0250 | 1038.91 | 1.138 | 2.11E-05 |
| Helium | 0.1567 | 5196.10 | 0.163 | 1.86E-04 |

THERMAL GAS FLOWMETER COMPRISING A GAS QUALITY INDICATOR

TECHNICAL FIELD

The present invention relates to the field of measurement of gas flows with thermal sensors. It begins with a method and a sensor for mass flow measurement according to the preamble of the independent claims.

STATE OF THE ART

In WO 01/96819 A1, a gas meter is disclosed which is calibrated as an energy meter. The calibration is based on the fact that sensor figure values are determined dependent upon the flow rate of a gauge gas or calibration gas and are stored in the form of a sensor gauge curve or sensor calibration curve in the gas meter. The sensor calibration curve or the sensor signal values are multiplied by a signal conversion factor and a calorific value factor for the basic gas mixture, so that the obtained product indicates a gas consumption in an output unit and after integration in an energy unit. With a further correction factor, the actual heat value of a supplied gas mixture can be taken into account at least approximately in the energy calibration. A measured heat value, averaged over a specific timespan, can be used as the actual heat value. It is disadvantageous that an external unit is required for determining the heat value.

In EP 0 373 965, a method and a device are disclosed for determining a gas or energy consumption from a corrected mass flow signal. During signal correction, the heat conductivity, specific heat capacity and density of the gas are taken into account. The corrected mass flow signal and hence the gas or energy consumption are dependent upon the gas type and in particular are identical for air, argon, helium, carbon dioxide, methane and propane. It is disadvantageous that a standardised mass flow signal of such a type is insensitive to the heat value of a gas or a gas mixture, since combustible gases with a different heat value (e.g. methane or propane) produce the same mass flow signals and even the same signals as non-combustible gases (e.g. helium, argon, carbon dioxide or air).

In the U.S. Pat. No. 5,311,447, a method and a device for combustionless determination of the specific heat value of natural gas is disclosed. For this purpose, specific heat value, density or proportion of inert gases are determined from measured values of viscosity, heat conductivity, heat capacity, optical absorption etc. by empirical formulae. The high measuring and computing complexity is disadvantageous in quantitative measurement of a plurality of independent gas type-dependent values and, when they are brought together, with a volume flow measurement in a gas meter for determining a consumed quantity of energy.

In WO 01/18500, an improved mass flowmeter with two CMOS anemometers is disclosed. On static gas, a heat conductivity is measured in the case of a constant heating capacity, and in the case of a pulsed heating capacity, a heat capacity is measured, the gas is identified and, from the specific heat value thereof together with the mass flow measurement, the total calorific value of the gas is determined. The relatively high complexity is again disadvantageous when determining the consumed quantity of energy from separate values of mass flow and specific heat value. In addition, the specific heat value for a sufficiently precise determination of the energy supply must be measured continuously and with great precision.

PRESENTATION OF THE INVENTION

It is the object of the present invention to indicate a method and a device for determining a flow rate, an improved calibration capacity being achieved. This object is achieved according to the invention by the features of the independent claims.

In a first aspect, the invention resides in a method for measuring a gas consumption by means of a gas meter, in particular for measuring a meterable gas energy supply in the private, public or industrial sphere, sensor signal values, which are essentially proportional to a flow rate, being determined by the gas meter by means of a thermal flow sensor and the sensor signal values being output as energy values on the basis of a calibration of the gas meter as energy meter, a gas type being determined by the gas meter insofar as a non-combustible gas mixture is differentiated from a combustible gas mixture and the gas meter, in the presence of a non-combustible gas mixture, is operated with a calibration in mass or standard volume units and, in the presence of a combustible gas mixture, with a calibration in energy units. The operation as energy meter also comprises calibration and operation as output meter with output of output values. The method and gas meter according to the invention presents various advantages. The reliability of the energy measurement is significantly increased since, with low complexity, a strict differentiation is made between high-quality useful gas and non-combustible gas while the gas is flowing. In particular, a differentiation is made automatically between a non-combustible calibration gas, typically nitrogen or air, and a basic gas mixture or gas to be measured and an automatic switch is implemented from a mass or volume scale to an energy scale. The same differentiation is effective also when out of operation, during operation, during manipulation of the meter or for another reason, so that falsification of the energy measurement by contact with air or similar is precluded. The operation with a calibration in mass, volume or energy units includes in particular a signal output and/or signal display in these units.

In a first embodiment, at least one gas type-dependent parameter of the gas mixture, in particular a heat coefficient, such as e.g. a heat conductivity $\lambda$ and/or heat capacity c or a viscosity $\eta$, are determined by means of a thermal gas quality sensor and, by comparison with known values of the parameter for known gases or gas mixtures, the gas mixture is identified as combustible or non-combustible. An approximate knowledge of the type or composition of the gas is therefore sufficient in order that a digital decision can be made between combustible/non-combustible and the corresponding calibration can be activated.

The embodiment according to claim 3 has the advantage of a particularly simple sensor configuration and signal evaluation. A summation of the temperature signals has the effect that the signal for determining a gas type-specific parameter or heat coefficient is independent of the flow direction and of possible asymmetries of the arrangement of the temperature sensors. A greater signal is also achieved than when using the temperature sensor alone which is placed upstream.

The embodiments according to claim 4 and 5 have the advantage that a simple computing specification suffices to categorise the gas or gas mixture which is present with high reliability as combustible and hence suitable for a meterable energy supply or as non-combustible and hence as a non-meterable mass flow.

The embodiments according to claim 6 have the advantage that the current requirement of the gas meter can be lowered effectively without losing measuring precision.

The embodiment according to claim 7 has the advantage that the entire gas energy consumption or energy supply can also be correctly determined when switching between the calibration in energy units and other flow units, such as mass or volume, has been implemented.

The embodiment according to claim 8 has the advantage that the flow measurement is continued optionally without interruption in mass or standard volume units, e.g. in order to determine a total volume flow, or is integrated only in the case of a flow of non-combustible gases, e.g. in order, when the gas circulation is closed, to generate a complementary control value for the supply of combustible gases or, after each switching of the calibration, it is re-initialised in order to document interruptions during the energy supply.

Embodiments according to claim 9 have the advantage in particular that manipulation attempts on the gas meter can be detected easily.

The embodiment according to claim 10 has the advantage that an automatic heat value tracking is implemented even without any external or internal determination of the current specific heat value of the gas or gas mixture.

In a second aspect, the invention resides in a gas meter with a thermal mass flow sensor for determining a gas energy supply according to the previously described method. The gas meter comprises a thermal flow sensor, is calibrated as energy meter in energy units and in addition as mass flowmeter in mass or standard volume units, has a gas quality sensor which generates a discrimination signal, in particular a gas type-dependent parameter or heat coefficient in order to differentiate a combustible gas mixture from a non-combustible gas mixture, and can be switched over on the basis of the discrimination signal between an operation as energy meter or as mass flowmeter. The gas meter is therefore calibrated for calibration purposes during storage or when out of operation as mass flowmeter or, with additional density measurement, as volume flowmeter and for measuring or metering purposes as energy meter. No metering takes place during operation if air is detected. Instead, a flow measurement can be implemented in mass or volume.

The embodiments according to claims 12-15 enable a particularly simple construction and operation of the gas meter. In particular, manipulation attempts on the gas meter during operation can be detected if a recurrent contact with air is detected.

Further embodiments, advantages and applications of the invention are revealed in the dependent claims and in the description and Figures which now follow.

SHORT DESCRIPTION OF THE DRAWINGS

Figure 2:
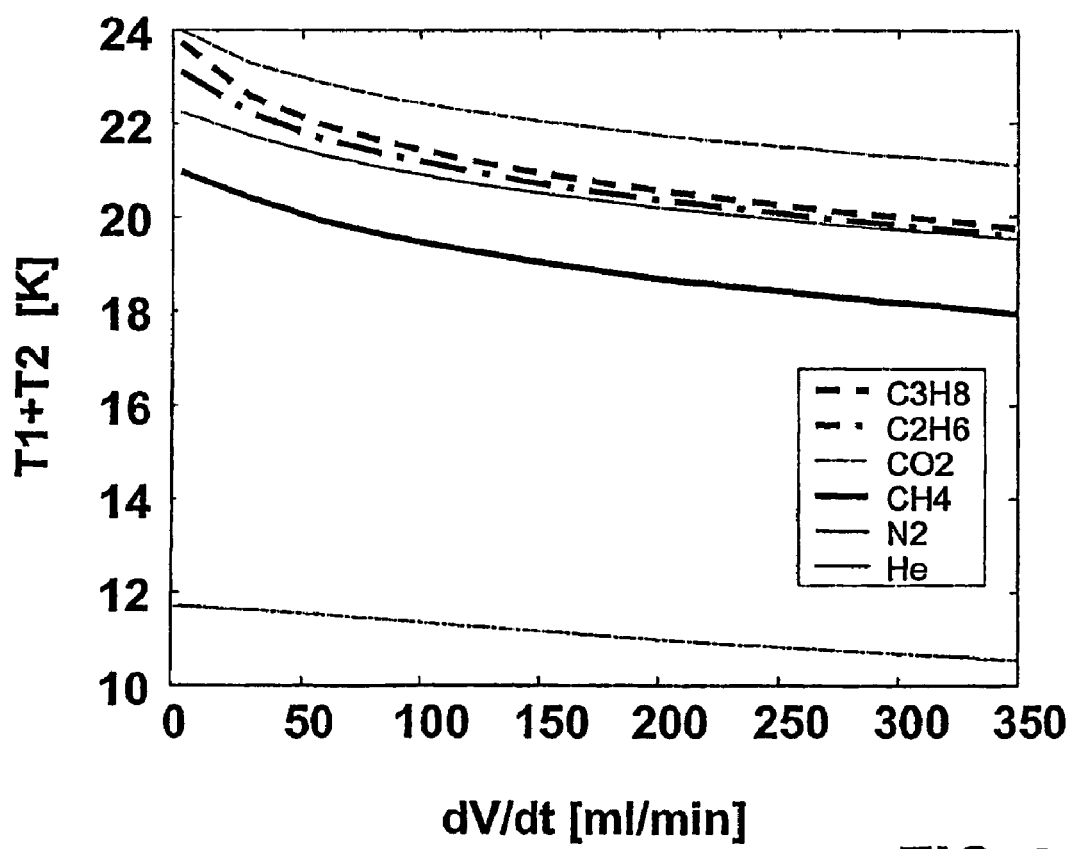
Figures 3, 4:
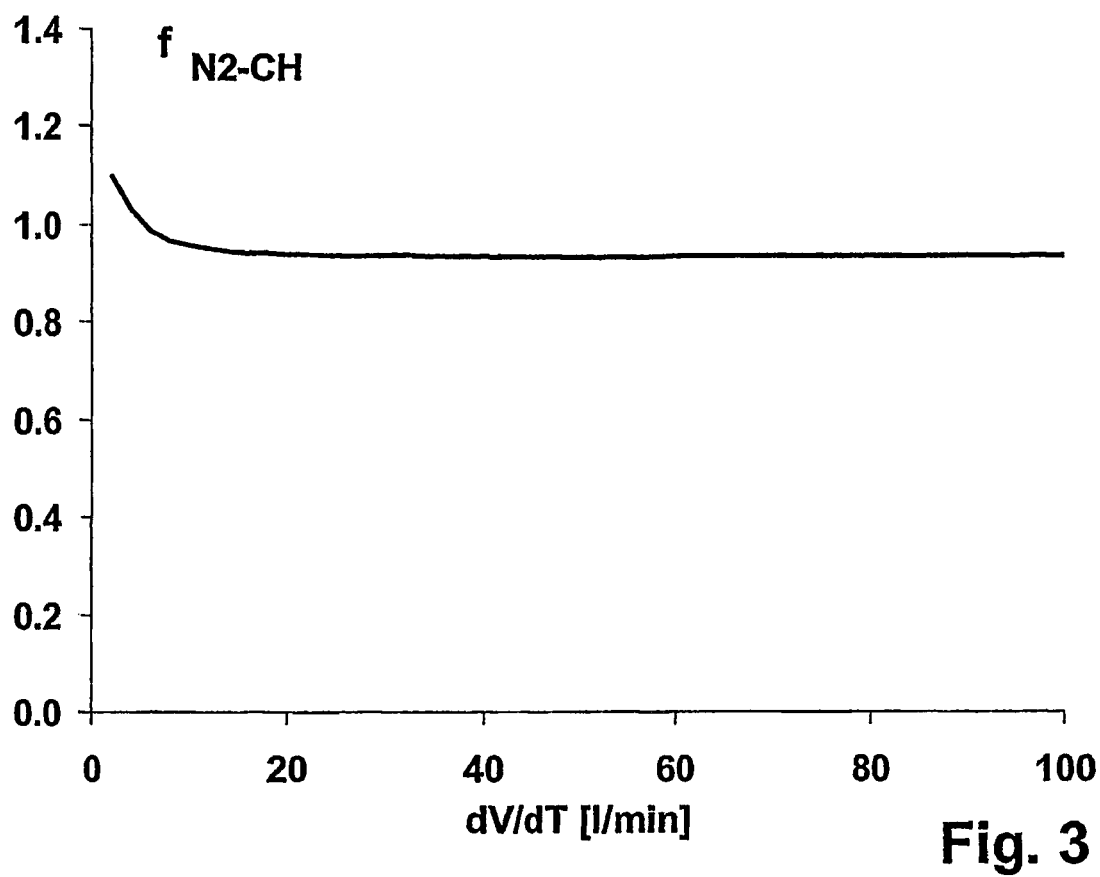

There are shown:

FIG. 1 in cross-section, a pipe, subjected to a flow, with a thermal flow sensor, which is a component of a gas meter with dual calibration according to the invention as energy and quantity meter;

FIG. 2 temperature summation signals for determining gas-specific heat transfer coefficients;

FIG. 3 a calibration curve for the transition between calibration gas and basic gas mixture (useful gas); and FIG. 4 a table with gas parameters for natural gas.

In the Figures, the same parts are provided with the same references.

WAYS OF IMPLEMENTING THE INVENTION

FIG. 1 shows a gas meter, comprising a thermal flow or mass flowmeter $1a$, $1b$, 7 which comprises a sensor element $1a$, which is disposed in a flow channel or pipe 2, a membrane $1b$ and a measuring and evaluating unit 7. A gas 3 with a flow and speed profile 4 flows in the pipe 2. The sensor element $1a$ is subjected to a flow velocity v to be measured. The flow sensor 1 comprises a heating element 6, a first temperature sensor $5a$ upstream and a second temperature sensor $5b$ downstream. From temperature signals $T_1$, $T_2$ of the temperature sensors $5a$, $5b$, a mass flow or standard volume flow signal $S_M$ can be determined in a known manner. The basic mode of operation is based on the fact that a temperature distribution through the flow 4, which is generated by the heating element 6, becomes asymmetric and a temperature difference $T_1-T_2$ at the temperature sensors $5a$, $5b$ is used as a measure of the flow velocity v or the mass flow dm/dT. To a good approximation, the mass flow signal $S_M$ is proportional to the temperature difference $T_1-T_2$. In the present case, in addition by the measuring means 7 from the mass flow signals $S_M$ or in general sensor signals S of the flow sensor $1a$, energy value signals $S_E$ are determined and output on the basis of a calibration of the gas meter 1 as energy meter. The calibration as energy meter is disclosed in WO 01/96819 A1, the content of which is included herewith in its entirety by reference in the present disclosure. Likewise, the three articles cited therein relating to the CMOS anemometer by J. Robadey and F. Mayer et al. are included by reference. The CMOS anemometer described there is particularly suitable as sensor element $1a$ of the flow sensor.

According to the invention, a gas type is determined by the gas meter 1 insofar as a non-combustible gas mixture 3 is differentiated from a combustible gas mixture 3 and the gas meter 1, in the presence of a non-combustible gas mixture 3, is operated with a calibration in mass or standard volume units, e.g. l/min and, in the presence of a combustible gas mixture 3, with a calibration in energy or output units, e.g. kWh.

For the operational capacity of the gas meter 1 as energy and mass flowmeter, instead of the flow sensor $1a$ with two temperature sensors $5a$, $5b$ and in particular instead of the CMOS anemometer $1a$, in general a thermal flow sensor can also be used in which the gas 3 is guided over a sensor element which has a heating means for temperature alteration and a sensor means for determining its temperature, the flow-dependent temperature alteration being in turn a measure of the mass flow. Alternatively, the thermal flow sensor $1a$ can also be operated with only one temperature sensor $5a$ which is disposed downstream. In general, the mass flow dm/dt can be indicated in mass or standard volume units, e.g. in kg/min or can be determined by means of the density ρ from a volume flow dV/dT according to dm/dt=ρ*dV/dT. In the gas meter 1, a signal output implies a signal display and/or a signal transmission to a reading or central evaluation unit (not illustrated).

According to WO 01/96819 A1, a sensor signal S is measured with a calibration gas 3, typically nitrogen $N_2$ or air, said sensor signal being essentially proportional to the standard volume flow rate $d(V_{N2,n})/dt$ of the calibration gas 3. By inversion of $Sd(V_{N2,n})/dt$, a sensor calibration curve F(S), previously designated by $F_n(Sd(V_{N2,n})/dt$, is determined and stored in the evaluating unit 7 of the gas meter 1. During operation, the sensor signal S is then calibrated by means of the sensor calibration curve F(S) to an (uncorrected) mass flow signal $S_m$ which is proportional to F(S) or simply $S_m=F(S)$. The calibration of the flow rate can therefore be expressed by a sensor calibration curve F(S) for the calibration gas under normal conditions. The mass flow rate signal $S_m$ still depends upon the type of gas. Deviations of the mass flow rate signal $S_m$ from an exact ideal value for a basic mixture, typically natural gas or in general a hydrocarbon mixture CH, are therefore corrected by a signal conversion factor or sensor signal correction factor $f_{N2-CH}$ (FIG. 3).

Hence, $S_M = S_m * f_{N2-CH} = F(S)$ applies with $S_m$=corrected mass flow rate signal. Finally an energy value signal $S_E$ is determined by multiplication with a heat value $H_{CH}$ (calorimetric value per unit of flow value, i.e. per standard volume or per mass) of the basis gas mixture and integration:

$$S_E = \int S_M \cdot H_{CH} \cdot dt = f_{N2-CH} \cdot H_{CH} \cdot \int F(S) \cdot dt.$$

Starting from this energy calibration for the basic gas mixture CH, it is now however no longer necessary to implement a measure of the current heat value of the gas mixture on the gas mixture. According to WO 01/96819 A1, an inherent automatic heat value tracking is effected namely in the thermal flow sensor 1a, in particular in the CMOS anemometer, in the case of deviations of the current gas mixture 3 from the basic gas mixture CH. It suffices therefore to attain an approximate knowledge relating to type and/or composition of the gas 3 and to make a digital decision as to whether a combustible or meterable gas 3 is supplied or else only a flow of a non-combustible or at least non-meterable gas supply is intended to be measured, in the first case a relatively reliable energy measurement, which relates to the current heat value, is effected without a heat value measurement.

According to WO 01/96819 A1 or the unpublished EP application No. 01 810 546.0, included herewith by reference in its entirety, suitable time averages can also be used for the mentioned values S, F(S), $f_{N2-CH}$ and $H_{CH}$ and values which can be derived therefrom.

Preferably, at least one gas type-dependent parameter $\lambda$, c, $\alpha$ (diffusibility), $\eta$ (viscosity) of the gas mixture 3, in particular a heat coefficient $\lambda$, c, $\alpha$, such as e.g. a heat conductivity $\lambda$ and/or a heat capacity c, is determined by means of a thermal gas quality sensor 1a and, by comparison with known values of the parameter $\lambda$, c, $\alpha$, $\eta$ for known gases or gas mixtures, the gas mixture 3 is identified as combustible or non-combustible.

In the following, a detailed analysis is provided for measuring the heat conductivity with the thermal flow sensor 1a. The gas 3 to be measured can be assumed to be extensively incompressible, since relative density alterations $\Delta\rho/\rho \approx \frac{1}{2}(v/c^o)^2$ with v=flow velocity and $c_0$=speed of sound for typical values $v \approx 3$ m/s and $c_0 \approx 300$ m/s are in the range of $10^{-4}$ and hence are negligible. For incompressible gases 3, i.e. $v \ll c_0$, and neglecting viscous dissipation, the heat conveyance including convection can be derived from the stationary heat output equation by addition of a convective term. For a flow channel 2 in the x-direction without heat source in the gas 3, the heat output equation with forced convention is $$\lambda \cdot \left( \frac{\partial^2 T}{\partial x^2} + \frac{\partial^2 T}{\partial y^2} + \frac{\partial^2 T}{\partial z^2} \right) = v_x \cdot c_p \cdot \rho \cdot \frac{\partial T}{\partial x} \quad \text{Eqn. 1}$$

with T=T(x, y, z) the stationary temperature field in the gas 3, $\lambda$=heat conductivity, $v_x$=flow velocity in the x-direction, $c_p$=heat capacity and $\rho$=density of the gas 3. For negligible convection $v_x \approx 0$, the heat conductivity $\lambda$ can be determined in that the stationary diffusion equation $$\lambda \cdot \left( \frac{\partial^2 T}{\partial x^2} + \frac{\partial^2 T}{\partial y^2} + \frac{\partial^2 T}{\partial z^2} \right) = 0 \quad \text{Eqn. 2}$$

is integrated and the correct boundary values for the integration constants (heat flow $j \neq 0$, no heat source in the gas 3) are used. For non-negligible convection $v_x > 0$, the inverse thermal diffusibility $\alpha^{-x} = c_p \rho / \lambda$ can be determined from the equation (Eqn. 1) when $v_x$ is known.

Equation (Eqn. 1) was solved with a finite element calculation for the flow sensor 1a according to FIG. 1 in CMOS configuration for typical gas components of natural gas (propane $C_3H_8$, ethane $C_2H_6$, carbon dioxide $CO_2$, methane $CH_4$, nitrogen $N_2$ and helium He) using their known heat coefficients $\lambda$, $c_p$, $\alpha$. In FIG. 2, the resultant temperature sum $T_1+T_2$ for these natural gas components is plotted as a function of the flow velocity $v_x$. The temperature sum $T_1+T_2$ for small $v_x$ (in the approximate range 0 . . . 20 ml/min, in particular 0 . . . 5 ml/min) are significantly differentiatable since the underlying heat conductivities $\lambda$ (see FIG. 4) have sufficiently different values. It suffices therefore, on the conventional flow sensor 1a, simply to use a summation signal of the temperature sensors 5a, 5b as a measure of a gas type and in particular as a gas discrimination signal for differentiating between a combustible and a non-combustible or non-meterable gas 3. Also from the temperature signal of the first temperature sensor 5a alone—and even from the less varying temperature signal of the second temperature sensor 5b alone—a gas type-dependent heat coefficient $\lambda$, c, $\alpha$ can be determined. In particular, it can always be determined, based on the heat conveyance in the flow direction, which temperature sensor 5a, 5b is the first, i.e. situated upstream, and which is the second, i.e. situated downstream. Also for greater flow velocities $v_x \gg 0$, the temperature curves $T_1+T_2$ or $T_1$ alone (not illustrated) are gas type-dependent and differentiatable since the underlying diffusibility values $\alpha$ and/or heat capacities $c_p$ or in general c are different. According to WO 01/18500, as mentioned initially, the heat conductivity $\lambda$ can also be measured on the static gas with a constant heat output and separately therefrom, in the case of a pulsed heat output, the heat capacity c or $c*\rho$ can be measured. For this purpose, the heating means with a constant heat output or operated in the form of heat pulses and a flow-independent heat conductivity $\lambda$ or heat capacity c can be measured at least temporally.

FIG. 4 shows a Table with heat coefficients $\lambda$, $c_p$, $\alpha$ and specific densities $\rho$ of typical natural gas components, methane, ethane, propane, oxygen, hydrogen, carbon monoxide (combustible) and carbon dioxide, nitrogen, water and helium (non-combustible). In a preferred embodiment, a measured heat conductivity $\lambda$ is tested for correspondence to a heat conductivity value corresponding to an absolute value of 0.026 W/mK for nitrogen, oxygen or air, in particular 0.0260 W/mK for nitrogen, 0.0263 W/mK for oxygen, or 0.0261 W/mK for air, or 0.0168 W/mK for carbon dioxide, a prescribable tolerance of ±10%, preferably ±5% and particularly preferred ±2%, being taken into account. In the case of correspondence, the gas mixture 3 is categorised as non-combustible and a signal output 8 of the gas meter 1 is operated with a scale 8b which is calibrated in mass or standard volume units, e.g. l/min. In the case of non-correspondence, the gas mixture 3 is categorised as combustible and a signal output 8 of the gas meter 1 is operated with a scale 8a which is calibrated in energy units e.g. kWh.

Alternatively or additionally, a measured heat capacity c or $c_p$ is compared with a threshold value corresponding to an absolute value of 1300 J/kgK, a prescribable tolerance of ±10%, preferably ±5% and particularly preferred ±2%, being taken into account. Upon falling below the threshold value, the gas mixture 3 is categorised as non-combustible and a signal output 8 of the gas meter 1 is operated with a scale 8b which is calibrated in mass or standard volume units. Upon exceeding the threshold value, the gas mixture 3 is categorised as combustible and a signal output 8 of the gas meter 1 is operated with a scale 8a which is calibrated in energy units.

Preferably, it is tested periodically whether the gas meter 1 is in contact with a combustible gas 3, in particular natural gas, or with a non-combustible gas, in particular nitrogen or air. Measuring intervals for determining sensor signals S; $S_m$, $S_M$, $S_E$ are chosen to be large, in the presence of a non-combustible gas mixture 3, in particular 1 minute or longer, and are chosen to be small in the presence of a combustible gas mixture 3, in particular 10 seconds or shorter.

A consumed supply of gas energy can be integrated in the gas meter 1 and, when switching the calibration to mass or standard volume units, can be stored intermediately and, when switching back to energy units, be used as start value. On the other hand, the flow rate $S_M$, when switching the calibration to energy units, can be further incremented and in particular output, or the integrated flow rate is stored intermediately and in particular output and, when switching back to mass or standard volume units, can be used as start value or be set back to zero as start value.

By means of an indicator or display 9, it can be displayed whether the gas meter 1 is in contact with air or natural gas or a mixture of air and natural gas. Furthermore, due to a default setting of the gas meter 1, mass or standard volume units can be indicated and energy units can be indicated only upon a first contact with useful gas, in particular natural gas. Also by means of a first initialisation of the gas meter 1, in particular during assembly, the calibration can be switched automatically from mass or standard volume units or air to energy units or natural gas. Finally, upon contact with air, natural gas and again air, a manipulation indicator 10 of the gas meter 1 can be activated.

The invention also has a gas meter 1 for implementing the above-described method for the subject. Preferably, the thermal flow sensor 1a and the gas quality sensor 1a have an identical sensor construction and in particular are identical. In the gas meter 1, the sensor signal values S; $S_m$, $S_M$, $S_E$ and a heat coefficient λ, $c_p$, α of the gas mixture 3 are then measured in the same thermal sensor 1a, in particular in a CMOS anemometer 1a with a heating wire 6 and with at least one temperature sensor 5a, disposed upstream, and optionally in addition with at least one temperature sensor 5b, disposed downstream. The thermal flow sensor 1a can be operated as a gas quality sensor 1a if a measured mass flow rate falls below a prescribable threshold value. Alternatively, the gas quality sensor 1a can be disposed in a region with a constant flow rate, in particular with extensively static gas 3.

According to FIG. 1, the gas meter 1 comprises: an indicator or a display 9 for gas quality, in particular for the presence of calibration gas 3 or useful gas 3, preferably air, natural gas or air/natural gas mixture; a manipulation indicator 10 which can be activated upon changing contact with a non-combustible gas 3, in particular calibration gas 3, a combustible gas or useful gas 3 and again a non-combustible gas 3, in particular an environmental gas 3, a measuring and evaluating unit 7 for determining energy consumption values (SE) and/mass flow rate values $S_M$; and preferably separate data memories 7b, 7c for storing energy consumption values $S_E$ and mass flow values or standard flow rate values $S_M$. The computing unit 7a also comprises a data memory for known heat coefficients λ, $c_p$, α, densities ρ or viscosities η of known gases and computing means for comparing measured heat coefficients λ, $c_p$, α, densities ρ or viscosities η with those stored or interpolated from stored values, and computing means for determining the gas mixture 3 as combustible or meterable or non-combustible or non-meterable.

REFERENCE LIST

- 1 Gas meter
- 1a Thermal mass flow sensor, CMOS sensor
- 1b Membrane
- 2 Flow channel, pipe
- 3 Gas; natural gas, gauge gas, calibration gas
- 4 Flow profile
- 5a, 5b First, second temperature sensor, thermoelements
- 6 Heating element, heating wire
- 7 Measuring and evaluating unit
- 7a Computing unit
- 7b Data memory for energy consumption values
- 7c Data memory for flow values
- 8 Signal output, display
- 8a Scale, calibrated in mass/standard volume units
- 8b Scale calibrated in energy units
- 9 Gas quality indicator, display
- 10 Manipulation indicator, display
- CH Natural gas, basic gas mixture
- $f_{N2-CH}$ Correction factor for sensor signal
- F(S) Sensor calibration curve
- $H_{CH}$ Heat value, calorific value
- λ Heat conductivity
- c, $c_p$ Specific heat capacity
- ρ Density
- α Diffusibility
- η Viscosity
- S Sensor signal
- $S_m$ Mass flow (rate) signal for gauge gas or calibration gas
- $S_M$ Mass flow (rate) signal for basic gas mixture
- $S_E$ Energy value signal
- $T_1, T_2$ Temperatures
- v, $v_x$ Flow velocity
- dV/dT Volume flow rate

The invention claimed is:

1. A method for measuring a meterable gas energy supply in the private, public or industrial sphere, utilizing sensor signals (S) that are proportional to a flow rate of the gas, the method comprising:

determining the signals using a gas meter by means of a thermal flow sensor, the sensor signals (S) being output as at least one of energy value signals ($S_E$) and corrected mass flow rate signals ($S_M$) based on a calibration of the gas meter as energy meter or a mass flow rate meter, wherein:

a) a gas type is determined by the gas meter insofar as a non-combustible gas mixture is differentiated from a combustible gas mixture;

b) the gas meter is operated with a calibration in mass or standard volume units (1/min) in the presence of a non-combustible gas mixture, and is operated with a calibration in energy units (kWh) in the presence of a combustible gas mixture;

c) at least one gas type-dependent parameter of the gas mixture is determined by means of a thermal gas quality sensor;

d) the gas mixture is identified as combustible or non-combustible by comparing the at least one gas type-dependent parameter with known values of the parameter for known gases or gas mixtures;

e) the thermal flow sensor provides the function of the gas quality sensor, the gas mixture being guided over a first temperature sensor, a heating element, and a second temperature sensor of the thermal flow sensor; and f) the corrected mass flow rate signals ($S_M$) are determined from a difference of temperature signals of the temperature sensors, and the gas type-dependent parameter is determined from a sum of the temperature signals or from the temperature signal of the first temperature sensor alone.

2. The method according to claim 1, wherein:
a) the thermal flow sensor determines a measured heat conductivity (λ) as the gas type-dependent parameter, which is tested for correspondence to a heat conductivity value corresponding to 0.0260 W/mK for nitrogen, 0.0263 W/mK for oxygen, 0.0261 W/mK for air, or 0.0168 W/mK for carbon dioxide, a prescribable tolerance of ±10% for each of nitrogen, oxygen, air, and carbon dioxide being taken into account,
b) in the case of correspondence, the gas mixture is categorized as non-combustible and a signal output of the gas meter is operated with a scale which is calibrated in mass or standard volume units (l/min), and
c) in the case of non-correspondence, the gas mixture is categorized as combustible and a signal output of the gas meter is operated with a scale which is calibrated in energy units (kWh).

3. The method according to claim 1, wherein the parameter is a measured heat capacity (c), which is compared with a threshold value corresponding to an absolute value of 1300 J/kgK, a prescribable tolerance of ±10% being taken into account,
b) upon falling below the threshold value, the gas mixture is categorized as non-combustible and a signal output of the gas meter is operated with a scale which is calibrated in mass or standard volume units (l/min), and
c) upon exceeding the threshold value, the gas mixture is categorized as combustible and a signal output of the gas meter is operated with a scale which is calibrated in energy units (kWh).

4. The method according to claim 1, wherein
a) it is tested periodically whether the gas meter is in contact with a combustible gas, or with a non-combustible gas, in and/or
b) measuring intervals for determining sensor signals (S) are chosen to be large, in the presence of a non-combustible gas mixture, and are chosen to be small, in the presence of a combustible gas mixture.

5. The method according to claim 1, wherein a consumed supply of gas energy is integrated in the gas meter; the consumed supply of gas energy is stored intermediately when switching the calibration to mass or standard volume units (l/min); and the consumed supply of gas energy is used as start value when switching the calibration back to energy units (kWh).

6. The method according to claim 1, wherein the corrected mass flow rate signals ($S_M$) are stored in mass or standard volume units (l/min) in the gas meter; and
a) the corrected mass flow rate signals ($S_M$) are further incremented when switching the calibration to energy units (kWh); and
b) the corrected mass flow rate signals ($S_M$) are stored intermediately, and are used as start values or are set back to zero as a start value when switching back to mass or standard volume units (l/min).

7. The method according to claim 1, wherein:
a) the gas meter displays whether it is in contact with a combustible gas, a non-combustible gas, or a combination thereof by means of an indicator or display;
b) mass or standard volume units (l/min) are indicated, and energy units (kWh) are indicated only upon a first contact with a combustible gas due to a default setting of the gas meter;
c) during assembly, the calibration is switched automatically from mass or standard volume units (l/min) for a non-combustible gas to energy units (kWh) for a combustible gas by means of a first initialization of the gas meter; and
d) a manipulation indicator of the gas meter is activated upon contact with a non-combustible gas, then a combustible gas, and then a non-combustible gas again.

8. The method according to claim 1, wherein:
a) sensor signals (S) dependent upon the flow rate of a calibration gas are determined for calibrating the gas meter as an energy meter and are stored in the gas meter in the form of a sensor calibration curve (F(S)), the sensor calibration curve (F(S)) being proportional to uncorrected mass flow rate signals (Sm) determined by the thermal flow sensor;
b) the corrected mass flow rate signals ($S_M$) are obtained by correcting the uncorrected mass flow rate signals (Sm) with a signal conversion factor; and
c) the energy value signals ($S_E$) are obtained from multiplying the corrected mass flow rate signals ($S_M$) with a heat value factor for a basic gas mixture, the energy value signals ($S_E$) indicating a gas consumption in energy units (kWh).

9. A gas meter for measuring a gas consumption according to claim 1.

10. A gas meter for measuring a meterable gas energy supply in the private, public or industrial sphere, the gas meter having a thermal flow sensor that is also used to determine a gas composition of the gas supply, and is calibrated in energy units (kWh) when used as energy meter, wherein:
a) the gas meter is calibrated in mass or standard volume units (l/min) when used as a mass flow rate meter;
b) the gas meter has a gas quality sensor which generates a discrimination signal, as a function of a gas type-dependent parameter in order to differentiate a combustible gas mixture from a non-combustible gas mixture; and
c) the gas meter can be switched between an operation as energy meter or an operation as a mass flowmeter based on the discrimination signal.

11. The gas meter according to claim 10, wherein the thermal flow sensor comprises CMOS anemometers with a heating wire and temperature sensors that are disposed upstream and downstream of the gas flow.

12. The gas meter according to claim 10, wherein
a) the thermal flow sensor can function as a gas quality sensor if a measured mass flow rate falls below a prescribable threshold value, or
b) the thermal flow sensor is disposed in a region with a constant flow rate.

13. The gas meter according to claim 10, wherein:
a) the gas meter has an indicator or a display for gas quality, which comprises the presence of a calibration gas, a combustible gas, a non-combustible gas, or a combination thereof;
b) the gas meter has a manipulation indicator that can be activated when the gas changes from a non-combustible gas to a combustible gas, and then back to a non-combustible gas;
c) the gas meter has a measuring and evaluating unit for determining energy consumption values ($S_E$) and/or mass flow values ($S_M$); and
d) the gas meter has separate data memories for storing energy consumption values ($S_E$) and mass flow rate values ($S_M$).

* * * * *